(12) United States Patent
Taillade et al.

(10) Patent No.: US 9,970,841 B2
(45) Date of Patent: May 15, 2018

(54) METHOD AND SYSTEM FOR MONITORING A CIVIL ENGINEERING CONSTRUCTION

(71) Applicants: SOLETANCHE FREYSSINET, Rueil Malmaison (FR); INSTITUT FRANCAIS DES SCIENCES ET TECHNOLOGIES DES TRANSPORTS, DE L'AMENAGEMENT ET DES RESEAUX, Champs-sur-Marne (FR)

(72) Inventors: Frédéric Taillade, Clamart (FR); Gilles Hovhanessian, Antony (FR); Nicolas Freitag, Orsay (FR)

(73) Assignees: SOLETANCHE FREYSSINET, Rueil Malmaison (FR); INSTITUT FRANCAIS DES SCIENCES ET TECHNOLOGIES DES TRANSPORTS DE L'AMENAGEMENT ET DES RESEAUX, Champs-sur-Marne (FR)

( * ) Notice: Subject to any disclaimer, the term of this patent is extended or adjusted under 35 U.S.C. 154(b) by 357 days.

(21) Appl. No.: 14/654,805

(22) PCT Filed: Dec. 18, 2013

(86) PCT No.: PCT/FR2013/053169
§ 371 (c)(1),
(2) Date: Oct. 9, 2015

(87) PCT Pub. No.: WO2014/096706
PCT Pub. Date: Jun. 26, 2014

(65) Prior Publication Data
US 2016/0146697 A1  May 26, 2016

(30) Foreign Application Priority Data
Dec. 20, 2012  (FR) ...................... 12 62393

(51) Int. Cl.
*G01M 5/00* (2006.01)
*G01R 31/11* (2006.01)
(Continued)

(52) U.S. Cl.
CPC ........ *G01M 5/0033* (2013.01); *G01M 5/0083* (2013.01); *G01N 17/008* (2013.01); *G01N 27/026* (2013.01); *G01R 31/11* (2013.01)

(58) Field of Classification Search
None
See application file for complete search history.

(56) References Cited

U.S. PATENT DOCUMENTS

| | | | | |
|---|---|---|---|---|
| 5,905,194 A | * | 5/1999 | Strong | G01M 3/18 324/532 |
| 2003/0016028 A1 | * | 1/2003 | Bass | F16L 53/007 324/642 |

(Continued)

FOREIGN PATENT DOCUMENTS

| DE | 10102577 C1 | 1/2001 |
|---|---|---|
| EP | 1830181 A1 | 9/2007 |

(Continued)

*Primary Examiner* — Melissa Koval
*Assistant Examiner* — Nasima Monsur
(74) *Attorney, Agent, or Firm* — Dentons US LLP

(57) ABSTRACT

A method for monitoring a civil engineering construction including a first metal reinforcement and a reference conductor element. The first metal reinforcement and the reference conductor being separated by dielectric material and each having a first end that is electrically accessible. The method including injecting an incident electrical signal which is applied differentially between the first ends of the first reinforcement and of the reference conductor element collecting reflected signals returning along the conductors in return, and analyzing the reflected signals by comparing (Continued)

them against reference signals in order to determine any potential structural defect in the first reinforcement.

18 Claims, 6 Drawing Sheets

(51) Int. Cl.
*G01N 27/02* (2006.01)
*G01N 17/00* (2006.01)

(56) References Cited

U.S. PATENT DOCUMENTS

| 2006/0086197 A1* | 4/2006 | Chen | G01M 5/0025 |
| | | | 73/862.451 |
| 2008/0024297 A1* | 1/2008 | Maki | G08B 13/124 |
| | | | 340/552 |
| 2010/0332163 A1* | 12/2010 | Surdon | G01R 31/085 |
| | | | 702/59 |

FOREIGN PATENT DOCUMENTS

| FR | 2972264 A1 | 3/2011 |
| JP | 08201324 A | 8/1996 |
| JP | 09288070 A | 11/1997 |
| JP | 1164176 A | 3/1999 |
| JP | 2009008521 A | 1/2009 |
| WO | 9427129 A1 | 11/1994 |
| WO | 2007135162 A1 | 11/2007 |

* cited by examiner

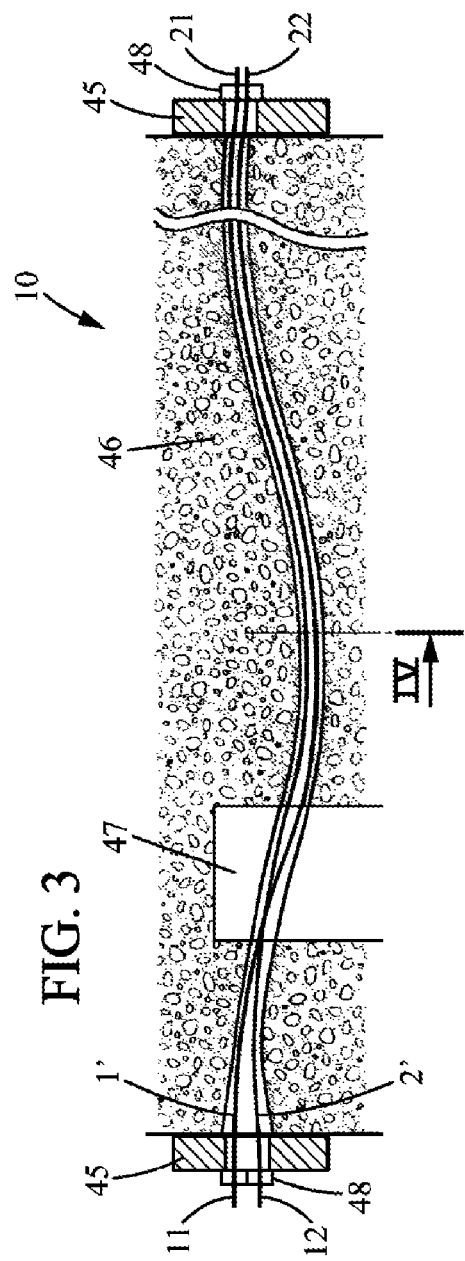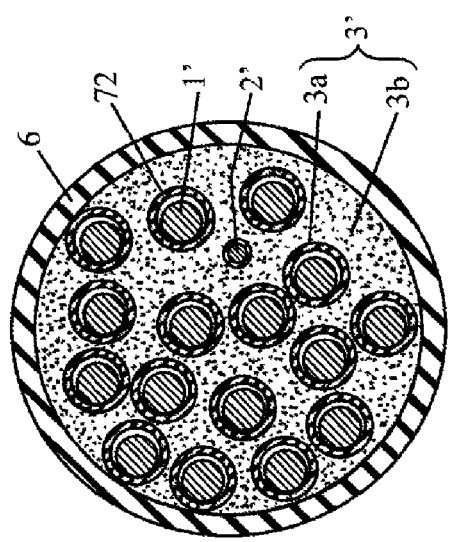

METHOD AND SYSTEM FOR MONITORING A CIVIL ENGINEERING CONSTRUCTION

This application is a National Stage Application of International Application No. PCT/FR2013/053169 filed Dec. 18, 2013, which claims priority from French Patent Application No. 1262393, filed on Dec. 20, 2012, each of which are hereby incorporated by reference in their entirety.

TECHNICAL FIELD

The present invention relates to the methods and systems for monitoring a civil engineering construction, in particular a construction comprising metal reinforcements.

PRIOR ART

The use of metal reinforcements is very commonplace in civil engineering constructions. For example, stressed metal cables are used to improve the mechanical properties of certain concrete constructions. Another example consists in placing metal strips or lattices in constructions of reinforced ground type. Yet another example consists in using metal strain carriers to maintain or stress a structure or a building.

The metal reinforcements made of steel exhibit very good mechanical properties but have the drawback of being subject to corrosion attacks. It is known practice to protect such metal reinforcements made of steel by a galvanization, a metal plating, a cathodic protection or by another passivation or cladding method. However, it appears necessary to monitor, over time, the state of health of such metal reinforcements, notably for the constructions for which the period of use can exceed several tens of years. It is preferable to be able to proceed with such monitoring non-intrusively, that is to say without directly intervening in the body of the construction.

Non-intrusive methods have already been proposed for monitoring the state of health of the metal reinforcements, notably based on the document FHWA-NHI-09-087, based on the sampling of reference test pieces or on resistive measurements. However, the resistive measurement methods do not make it possible to identify a local structural defect like a local loss of material or a nick which can take place in one or more reinforcements of the construction. For its part, the sampling of reference test pieces provides only fragmented information, and many existing constructions are not provided with such test pieces.

There has therefore emerged a need to improve the known non-intrusive solutions for monitoring the state of health of the metal reinforcements and be able to detect a potential structural defect linked to corrosion and/or ageing for example.

SUMMARY OF THE INVENTION

To this end, according to the present invention, a method is proposed for monitoring a civil engineering construction, comprising at least one first metal reinforcement contributing to the mechanical strength of said construction, and a reference conductor element, forming, with the first reinforcement, a pair of two conductors, said two conductors being separated by dielectric material over a part of their length, said dielectric material being formed by a construction or filling material, the first reinforcement and the reference conductor element each having an electrically accessible first end, the method comprising:

A—injecting at least one incident electrical signal applied differentially between the first ends of the first reinforcement and of the reference conductor element, B—collecting reflected signals returning along the conductors, measured between the first ends of the first reinforcement and of the reference conductor element, C—analyzing the reflected signals, to deduce therefrom the presence of a localized potential structural defect on the first reinforcement, and the location of this defect along the first reinforcement.

By virtue of these provisions, the properties of propagation of the signals along the conductors are used, and it is possible to identify a structural defect, even highly localized or present at places over the length of the reinforcement; it is also possible to identify the position of such a potential defect along the reinforcement; it is further possible to identify an alteration of the length of the reinforcement, for example due to a break or to a totally corroded portion.

In various embodiments of the invention, it is possible if necessary to further make use of one and/or other of the following provisions, taken in isolation or in combination:

the reflected signals are compared to reference signals; thereby, reference signals are used without using absolute comparison elements;

the reference conductor element can be formed by an element not subject to corrosion; thereby, this element not subject to corrosion is an unalterable test piece and a potential defect revealed by the reflected signals can be attributed unambiguously to the first reinforcement;

the reference conductor element can be formed by a second reinforcement; such that the method can be implemented on pre-existing constructions, the method then using only original metal reinforcements;

the reflected signals are compared to previously recorded reflected signals; such that it is possible to conduct a monitoring over time of the characteristics and of the state of health of the reinforcement as a function of the ageing of the construction;

the reflected signals are compared to reflected signals relating to another pair of conductors; thereby, it is possible to conduct a monitoring in the space of the construction, and in particular it is possible to use relative measurements to identify the most damaged reinforcements out of a plurality of reinforcements, but also to assess the state of ageing of the construction from the level of uniformity of these comparative measurements;

a time reflectometry method can be used to analyze and compare the reflected signals; thereby, it is possible to determine the position of a structural defect over the length of the reinforcement;

the incident electrical signal can comprise a plurality of predetermined frequency components and the frequency components of the reflected signals are analyzed; thereby, such a frequency analysis is a more robust method than a pure temporal method;

the method can further comprise a preliminary step before the step A—: A0—providing access to establish an electrical contact with each of the first ends of the first reinforcement and of the reference conductor element; thereby, it is possible to use the method on existing constructions, including old constructions;

the method can further comprise a complementary step in which access is provided to the second ends of the two conductors, signals transmitted along conductors to said second ends are collected there and said transmitted signals are analyzed with reference to reference transmitted signals; thereby the detection of localized structural defects can be made more reliable by the complementarity of the analysis of the reflected signals and of the transmitted signals;

the construction is a reinforced ground/soil construction, the dielectric material being formed by the ground, the reinforcements extending mainly in a longitudinal direction from a construction facing, and being substantially parallel spaced apart by a distance D, said reinforcements being, for example, geotechnical nails or strain carriers (anchors ties); such that it is possible to apply the method to many reinforced ground constructions, including already existing ones;

the construction can comprise a facing and a filling, and can comprise a succession of beds of reinforcements of which at least a part is connected to the facing and of ground layers put in place by filling and compacting said filling, said reinforcements being, for example, smooth or ribbed metal strips; thereby, the application of the method is particularly suited to facing-based and filled-ground reinforced ground constructions;

the reinforcements are mechanically connected to the facing, and an auxiliary electrical conductor makes it possible to electrically link each reinforcement to an electrical contact accessible from the outer surfacing of the facing; such that the facing plates can be prearranged for easy implementation of the method;

the reinforcements have a length of between 2 m and 20 m and the distance D is between 0.2 m and 3.0 m; such that the method can be used for a wide variety of reinforcements and of constructions;

the construction can comprise a prestressing duct comprising at least one prestressing metal cable forming the first reinforcement, and an electrical conductor forming the reference conductor, separated by a filling mortar, said electrical conductor being, for example, a sheathed electrical wire; it is thus possible to apply the method to prestressing cable systems for constructions of prestressed concrete.

The present invention relates also to a system for monitoring a civil engineering construction, comprising, on the one hand, a civil engineering construction comprising at least one first metal reinforcement contributing to the mechanical strength of said construction and a reference conductor element forming, with the first reinforcement, a pair of two conductors separated by dielectric material over a part of their length, said dielectric material being formed by a construction or filling material, and, on the other hand, an electronic apparatus configured to emit an incident signal applied to the ends of a pair of two conductors and to collect the reflected signals measured at the terminals of the ends of the pair of two conductors, and to analyze the reflected signals so as to deduce therefrom the presence of a localized potential structural defect (9) on the first reinforcement, and the location of this defect along the first reinforcement; thereby, it is possible to apply the above method non-intrusively and identify the position of such a potential defect along the reinforcement.

Furthermore, the electronic apparatus can comprise a network analyzer; such that an analysis by frequency reflectometry can be implemented.

BRIEF DESCRIPTION OF THE DRAWINGS

Other aspects, aims and advantages of the invention will become apparent on reading the following description of its embodiments of the invention, given as nonlimiting examples. The invention will also be better understood in light of the attached drawings in which:

FIG. 3 is a schematic view in cross section of a construction of prestressed concrete structure type representing a second embodiment in which the method according to the invention can be implemented, FIG. 4 shows a detail in transverse cross section along the cutting line IV-IV in FIG. 3.

DETAILED DESCRIPTION OF THE INVENTION

In the different figures, the same references denote identical or similar elements.

Figure 1:
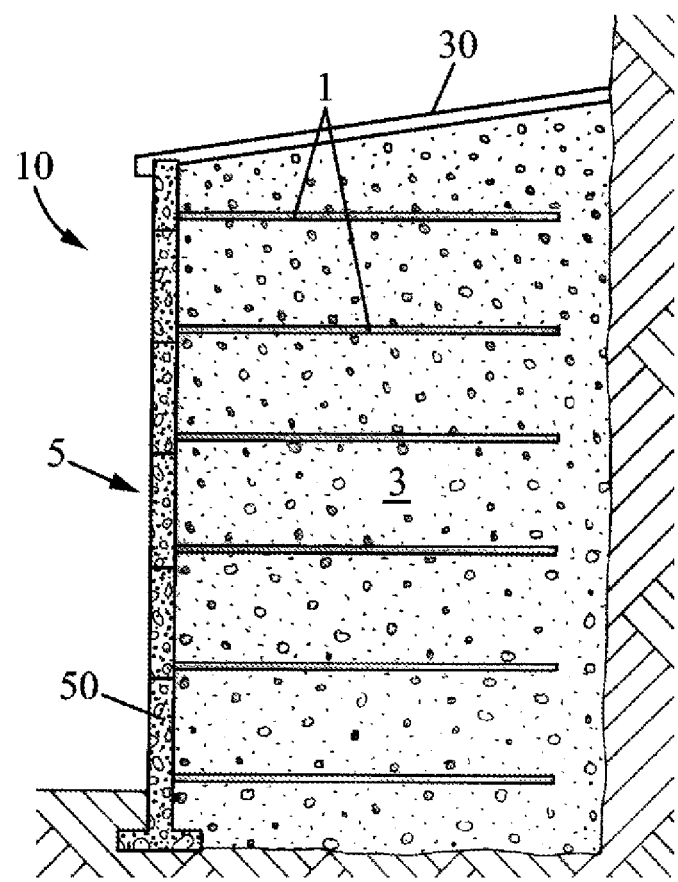
FIG. 1 is a schematic view in cross section of a construction of reinforced ground type in which the method according to the invention can be implemented.

FIG. 1 shows a construction 10 of reinforced ground type, comprising a facing 5, constructed for example based on prefabricated concrete panels 50, and a filling area 3 formed by earth, sand, gravel or any construction materials available to form the filling area 3.

Said filling area is reinforced by metal reinforcements 1 as known in the art, the metal reinforcements being able to be connected to the facing 5 in a known manner.

In practice, this kind of construction is built by successive layers; prefabricated facing panels are installed to a certain height, a plurality of reinforcements 1 are installed at the same horizontal level, that is called a "bed" of reinforcements, that are each anchored into the opposite facing panel; then, filling material 3 is added on top of the installed metal reinforcements to a height close to the top portion of the installed facing panels; if necessary, the filling material is packed down with a compacting machine. The preceding operations are repeated layer after layer up to the height planned for the construction.

This type of construction can be, by way of example, a dam, a dyke, a bridge abutment, a bedrock of a railway line or roadway, a canal bank, a construction for retaining various fluids and/or leachate-emitting substances, a construction intended to widen or raise an existing construction, an embankment circumscribed by a facing or, more generally, any other civil engineering construction.

This type of construction can be covered over its top portion by a coverage 30 intended to prevent the ingress of run-off or precipitation fluids directly into the filling 3 of the construction.

The above-mentioned reinforcements 1 are in practice made of galvanized steel which proves to be the best trade-off in terms of mechanical properties and corrosion resistance. However, this type of construction generally has a very long period of use, typically greater than several tens of years. This period of use is generally without degradation of the level of safety but, in some cases, external factors may adversely affect the durability of the reinforcements.

The metal reinforcements of galvanized steel may then be subject to corrosion attacks which can vary in the space of the construction and in time. In particular, the area close 31 to the facing 5 can be subject to greater corrosion attacks than the body of the filling. Similarly, depending on weather conditions and/or the seasons, the construction may be subject to run-off of de-icing salts, or other particularly corrosive chemical products, in particular in the cases where the coverage 30 is absent or does not correctly fulfill its role.

It follows that the corrosion may not be uniform in space and in time, and it may provoke highly localized defects.

Consequently, it has become important to monitor the good condition of the metal reinforcements 1 in order to ensure that their condition can guarantee the mechanical properties of the construction throughout its period of use.

Advantageously, according to the present invention, the condition of the reinforcements is monitored by a non-intrusive method.

Figure 2:
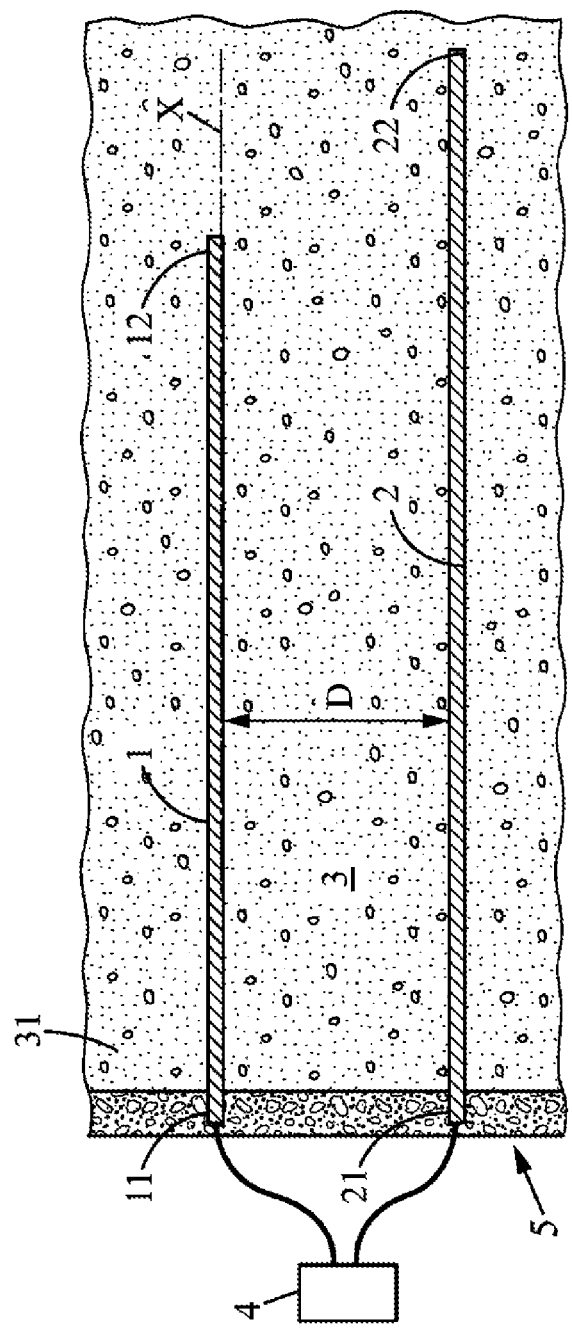
FIG. 2 is a more detailed view of the construction of FIG. 1.

As represented in FIG. 2, which shows a pair of adjacent reinforcements out of the plurality of reinforcements contained in the construction, an electronic apparatus 4 is used that is electrically connected to the two reinforcements represented, of which at least one contributes the mechanical strength of the construction. The two reinforcements represented may be one on top of the other, one alongside the other, askew or in any other arrangement, even not mutually parallel or not at right angles to the facing.

The electronic apparatus 4 is intended to inject at least one incident electrical signal at the terminals of a pair of adjacent reinforcements 1, 2 in the filling area, the signal injection being done preferentially in differential mode. The filling material 3 or construction material which separates the two reinforcements 1, 2 constitutes a dielectric material whose relative permittivity varies with the consistency and/or the dampness of the filing material and/or other secondary parameters.

In the example illustrated, each of the two reinforcements 1, 2 extends in the axial direction X at right angles to the surfacing of the facing, between a first end 11, 12 at the level of the facing and a second end 21, 22 opposite the first and situated in the body of the filling.

The two reinforcements 1, 2 are separated by a distance D, which can typically lie within an interval of 0.2 m to 3 m, preferentially between 0.5 m and 1 m, and even more preferentially between 0.7 m and 0.8 m. It should be noted that, once the construction is built, the relative position of the two reinforcements 1, 2 does not change over time.

The two reinforcements 1, 2 can have different lengths or, preferably, a similar length, the method being able to be implemented in both cases. The reinforcements can take the form of smooth or ribbed metal strips, with a thickness of a few millimeters, for example 5 mm, and a width of a few centimeters, for example 5 cm.

The two reinforcements 1, 2 are electrically conductive and form a pair of conductors. This pair of conductors forms, with the dielectric material 3 of the filling, an electrical transmission line to which a reflectometry method is applied.

Figure 6:
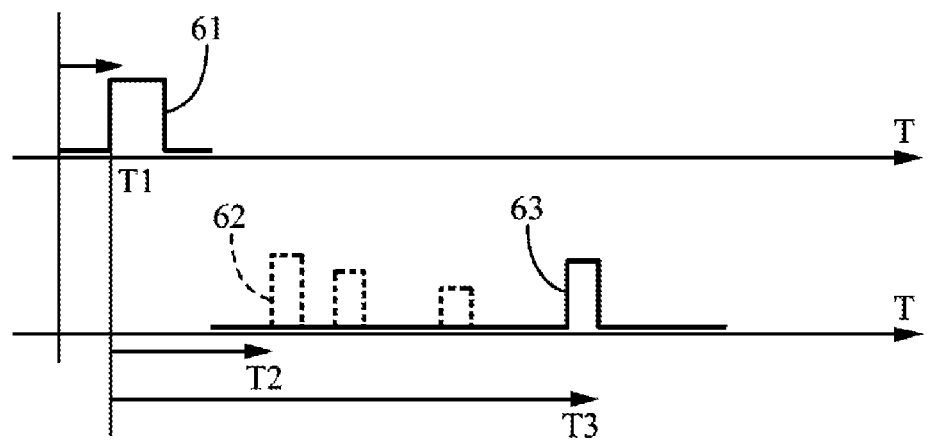
FIG. 6 shows an example of timing diagrams of the signals implemented.

More specifically, referring to FIG. 6, the method typically comprises the steps of:

A—injecting an incident electrical signal 61 applied differentially between the first ends 11, 21 of the reinforcements 1, 2,
B—collecting reflected signals 62, 63 returning along the conductors, measured between said first ends,
C—analyzing the reflected signals, to deduce therefrom a localized potential structural defect 9 on the first reinforcement.

In the step C—, advantageously, the reflected signals can be compared to reference signals, without reference to absolute comparison elements.

Furthermore, it is possible to deduce therefrom the presence of a localized potential structural defect 9 on the first reinforcement, and the location of this defect along the first reinforcement.

Working on a pair of reinforcements, that is to say on a pair of conductors, in differential mode, has proven fruitful whereas attempts made by injecting a signal on a single reinforcement have not led to satisfactory results.

The electronic apparatus 4 can consist of an association of a pulse generator and a signal analyzer (digital oscilloscope plus post-processing), for example in the case of use of time reflectometry, or else the electronic apparatus 4 can be formed by a network analyzer for example in the case of use of frequency reflectometry.

The reference signals mentioned in the step C—can correspond to signals reflected by a pair of reinforcements in the new state, for a plurality of relative permittivity values of the filling material, for example for relative permittivity values ranging from 1 to 80 (for example, the value 7 for a cement mortar). According to an alternative, said reference signals can be signals measured on this particular pair of reinforcements while the construction was in its initial state, and the effect of the variation of relative permittivity can be taken into account by computation or extrapolation based on previous results.

The second reinforcement 2 can be formed by a reference conductor element not necessarily contributing to the mechanical strength. In a particular case, this reference conductor can be chosen not to be subject to corrosion and thus form an unalterable test piece, in which case any defects will be attributed unambiguously to the first metal reinforcement 1.

Figure 5:
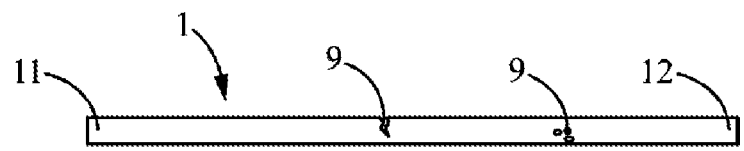
FIG. 5 shows a reinforcement affected by a structural defect.

Referring to FIG. 6, which illustrates an example of timing diagrams relating to a time reflectometry method, the incident electrical signal 61 is injected at the instant T1. In normal time, the signal reflected by the pair of reinforcements simply comprises an echo 63 returning to the first ends at the instant T3, which corresponds to the reflection on the second end 12. In the case of the presence of a localized structural defect 9, as illustrated in FIG. 5, additional echoes 62 (drawn in dotted lines) return to the first ends at the instant T2 in the example illustrated, generally before the normal main echo. The temporal position of the echo at the instant T2 makes it possible to identify and locate the presence of a defect 9 along the reinforcement 1. Moreover, the temporal position of the main echo at the instant T3 makes it possible to check that the length of the reinforcement (or of the two reinforcements) has not been modified.

The incident electrical signal 61 can be a short frame comprising a number of frequency components, or can be like a pulse of 'Dirac' type, even like a train of single-frequency pulses, this list not being exhaustive.

In an alternative frequency reflectometry method (not represented in the figures), the incident electrical signal 61 comprises a plurality of different frequency components. The spectral analysis of the reflected signals, in comparison to reference spectra, makes it possible to detect an abnormal condition of the reinforcement and deduce therefrom the presence of one or more anomalies.

In particular, the collection of the reflected signals can occur simultaneously with the injection of the incident signal.

As a nonlimiting example, it will be possible to use frequency components lying between 5 kHz and 9 GHz. This choice can be made more accurately if the nature of the dielectric material is well known or does not change over time.

The presence of defect(s) provokes a modification of the frequency spectrum; expected absorption peaks may have been moved in frequency, or new absorption peaks may occur.

Reference spectra that have been measured on the construction when the latter was new can serve for reference; in addition, typical spectrum modifications linked to 'simple' defects (break) can also be included in a database of reference spectra.

The appearance of unexpected spectral rays makes it possible to identify a possible structural defect; the intensity and the spread of this unexpected ray makes it possible to locate the presence of a defect 9 along the reinforcement 1.

An apparatus of network analyzer type is conventionally used for the spectrum acquisitions.

Of course, it will be possible to use a combination of the two methods, time and frequency, in order to increase the accuracy of the measurements performed.

The method can be implemented for existing constructions, recent or older by a few years. In this particular case, it will be possible to drill the concrete panel 50 from the frontage to reach the anchor in order to electrically connect the electronic apparatus 4 to the reinforcement housed in the filling.

Figure 7:
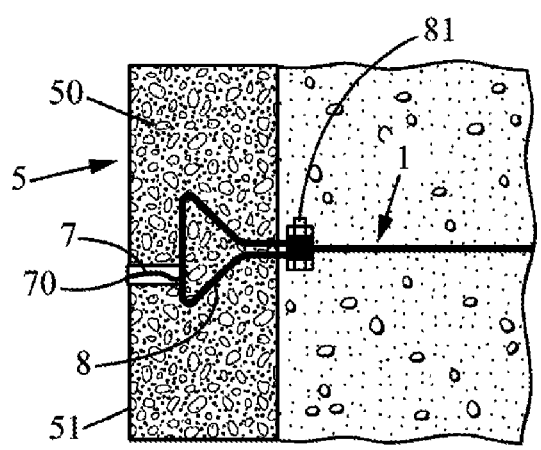
FIG. 7 shows a detailed view in cross section of a facing element of the construction of FIG. 1.

The method concerned can also be applied to a new construction, in which case a prearrangement of the concrete panels 50 will be provided, as is illustrated in FIG. 7. More specifically, the reinforcement 1 is intended to be mechanically coupled to an anchor 8 inserted in the casting of the concrete panel 50. Furthermore, an electrical connection in the form here of a conductor 7 electrically connects the anchor 8 with a connection terminal 70 arranged in the vicinity of the outer frontage of the facing 5. This connection terminal 70 can be housed in a connector protected from the environment notably from bad weather, which can be received in a hollow formed in the frontage of the facing 5. The anchor 8 is electrically connected to the reinforcement 1 by the bolted link 81.

In another embodiment represented in FIGS. 3 and 4, the method described above is used with application to a prestressing device of a prestressed concrete construction. A prestressing duct 6 contains a plurality of metal cables, said metal cables being able to be sheathed or unsheathed.

Each sheathed metal cable comprises a metal core 1', if appropriate inside a protective sheath 72, 3a made of synthetic material, which can be filled with grease, according to the cases of application. The prestressing duct 6 further includes at least one reference metal conductor 2', in this case a copper wire sheathed with a protective synthetic insulator. After insertion of the metal cables and of the reference conductor or conductors, a cement mortar 3b is injected into the duct which solidifies after a certain time, such a cement mortar 3b constitutes, with the protective sheath 3a if present, a dielectric material 3' which separates the sheathed metal cables 1' and the reference conductor or conductors 2'.

At each of the ends of the prestressing duct 6, there is arranged a bearing plate 45 on which gripper systems 48 come to bear, anchored on the tensioned metal cables as is known in the art.

In this embodiment, access to the second ends of the reinforcements 21, 22 is possible, and consequently the method can include a step of analysis of signals transmitted to this second end. Just as in the case of signals reflected toward the first end 11, 12, the analysis of the signals transmitted to the second end 21, 22, in particular the analysis of the differences relative to reference transmitted signals, makes it possible to identify the presence of a possible defect, even highly localized, in the metal reinforcement 1, 2.

In certain particular cases like those of a nuclear containment enclosure, the second ends 21, 22 and the first ends 11, 12 can be located in proximity, which in practice facilitates the implementation of the abovementioned aspect.

It should be noted that the dielectric material 3' is not necessarily uniform over the length of the reinforcements: in the example of FIG. 3, the prestressing duct includes a portion surrounded by concrete 46 and another portion surrounded by air 47.

Obviously, in this embodiment, the reference conductor 2' can also be a metal cable and the method can be applied to any pair of existing prestressing metal cables in a prestressing duct already installed in a construction.

Figure 8:
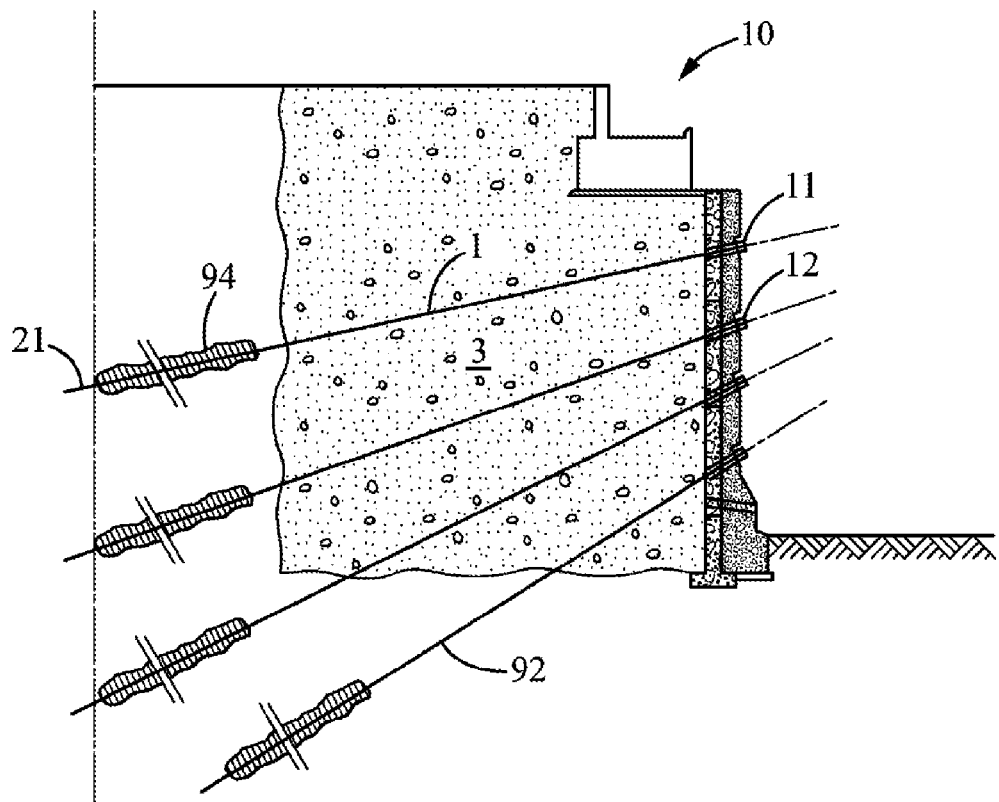
FIG. 8 illustrates the method that is the subject of the invention.
Figure 9:
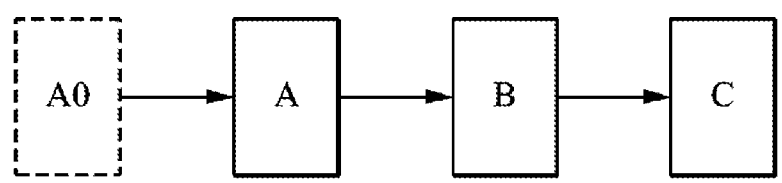
FIG. 9 is a schematic view in cross section of a construction stabilized by geotechnical tie rods representing a third embodiment in which the method according to the invention can be implemented.

In another embodiment represented in FIG. 8, a geotechnical reinforcement system can be used, for which metal ties 92 can be installed to form reinforcements in a construction to be consolidated Said ties are placed at a distance from one another and not necessarily mutually parallel; the first end is accessible on the frontage of the facing or of the wall of the construction; in effect, the tie is bolted to bear on a bearing plate. A sealing cement 94 is poured around the second end of the tie which, by solidifying, ensures an anchorage in the surrounding structure.

In another embodiment not represented in the figures, the reinforcements can take the form of ties passing through a construction to be consolidated. In this case, access is possible at both ends, which makes it possible to work both on the reflected signals and on the transmitted signals as already indicated above in the case of the prestressing duct.

Figure 10:
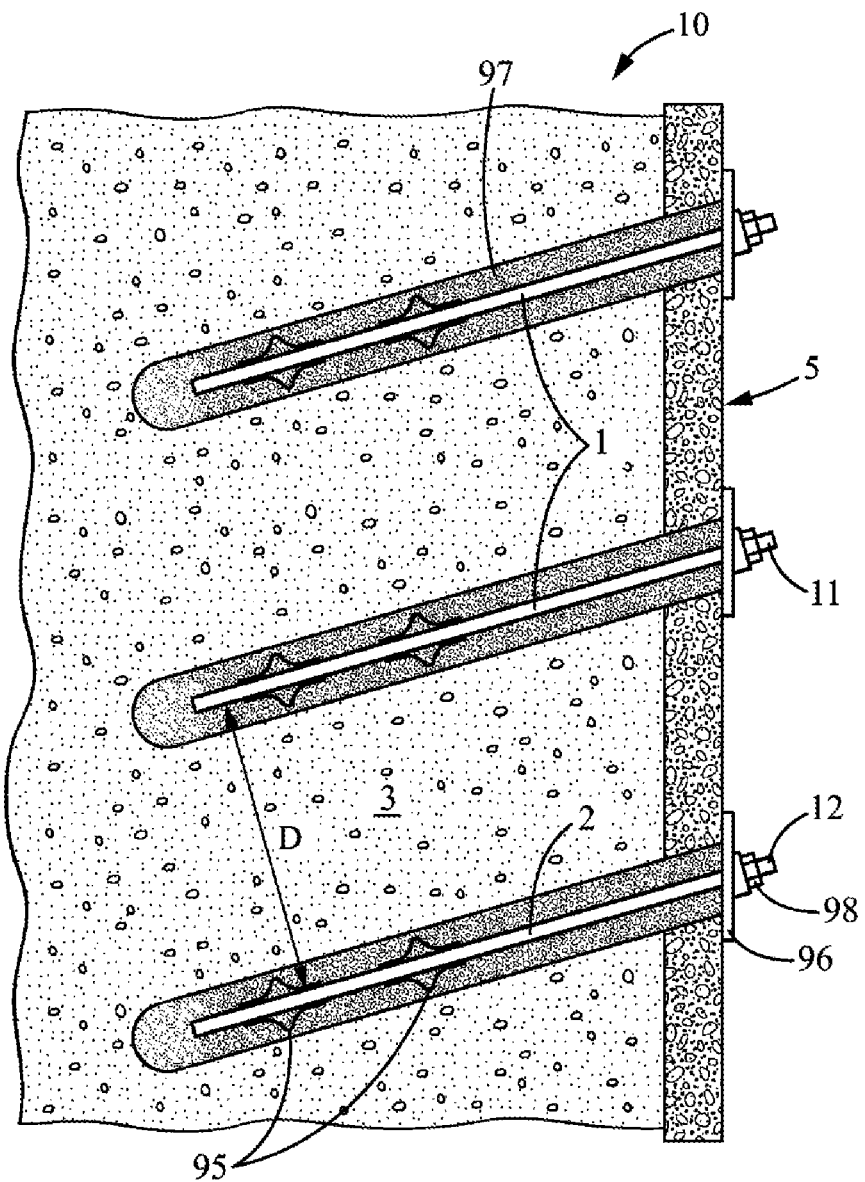
FIG. 10 is a schematic view in cross section of a construction stabilized by geotechnical nailing representing a fourth embodiment in which the method according to the invention can be implemented.

In yet another embodiment represented in FIG. 10, a geotechnical nailing system can be used, for which metal rods, called 'geotechnical nails' (anchor rods), are installed; these nails form metal reinforcements 1, 2 in a manner analogous to the description of the preceding examples, and are separated by the filling or construction body forming a dielectric material. Onto said nails, collars 95 are fixed extending radially from the metal rod. A cement mortar 97 is injected into the cavities where the nails are installed. A pressure plate 96 is arranged outside the facing 5, this plate is pressed against the facing by a screwing system 98, here in the form of a nut which comes to be screwed onto the threading provided on the end 11 of the nail.

It should be noted that, even if the second ends 21, of the reinforcements are in electrical contact, the method for implementing the invention can even so be used.

It should be noted that, in the case where only metal reinforcements contributing to the mechanical strength (without unalterable indicator) are used, the method can use a successive comparison of a number of pairs of reinforcements in order to identify whether an encountered defect can be attributed to the first or the second reinforcement of a pair considered.

The invention claimed is:

1. A method for monitoring a civil engineering construction being a reinforced ground construction with a construction facing and a plurality of metal reinforcement, the reinforced ground construction comprising at least one first metal reinforcement contributing to the mechanical strength of said construction, and a reference conductor element, forming, with the first reinforcement, a pair of two conductors, said two conductors being separated by dielectric material over at least a part of their length, said dielectric material being formed by earth, sand, gravel, or a combination thereof as filling material, the reinforcements extending mainly in a longitudinal direction (X) from the construction facing, and being substantially parallel and spaced apart by a distance D being comprised between 0.2 m and 3 m, the first reinforcement and the reference conductor element each having an electrically accessible first end connected to the facing, the method comprising:
A) injecting at least one incident electrical signal applied differentially between the first ends of the first reinforcement and of the reference conductor element,
B) collecting reflected signals returning along the conductors, measured between the first ends of the first reinforcement and of the reference conductor element, and
C) analyzing the reflected signals, to deduce therefrom the presence of a localized potential structural defect on the first reinforcement, and the location of this defect along the first reinforcement.

2. The method as claimed in claim 1, wherein in the step C, the reflected signals are compared to reference signals.

3. The method as claimed in claim 1, wherein the reference conductor element is formed by an element not subject to corrosion.

4. The method as claimed in claim 1, wherein the reference conductor element is formed by a second reinforcement.

5. The method as claimed in claim 1, wherein the reflected signals are compared to previously recorded reflected signals.

6. The method as claimed in claim 1, wherein the reflected signals are compared to reflected signals relating to another pair of conductors in the same construction.

7. The method as claimed in claim 1, wherein a time reflectometry method is used to analyze or compare the reflected signals.

8. The method as claimed in claim 1, wherein the incident electrical signal comprises a plurality of predetermined frequency components and the frequency components of the reflected signals are analyzed.

9. The method as claimed in claim 1, further comprising a preliminary step before the step A:
A0) providing access to establish an electrical contact with each of the first ends of the first reinforcement and of the reference conductor element.

10. The method as claimed in claim 1, wherein access is provided to the second ends of the two conductors, signals transmitted along conductors to said second ends are collected and said transmitted signals are analyzed with reference to reference transmitted signals.

11. The method as claimed in claim 9, wherein the construction comprises a succession of beds of reinforcements of which at least a part is connected to the facing and of ground layers put in place by filling and forming said filling, said reinforcements being, for example, smooth or ribbed metal strips.

12. The method as claimed in claim 11, wherein an auxiliary electrical conductor makes it possible to electrically link each reinforcement to the electrical contact accessible from the outer surface of the facing.

13. The method as claimed in claim 11, wherein the reinforcements have a length of between 2 m and 20 m.

14. The method as claimed in claim 1, wherein each of the electrical contacts is electrically coupled to the reinforcement via an anchor inserted in the casting of a concrete panel forming part of the facing, said anchor mechanically coupling the reinforcement to the facing.

15. A system for monitoring a civil engineering construction, the system comprising:
a civil engineering construction being a reinforced ground construction with a construction facing; and
a plurality of at least four reinforcement installed in a filing material, the reinforced ground construction comprising:
at least one first metal reinforcement contributing to the mechanical strength of said construction and a reference conductor element forming, with the first reinforcement,
a pair of two conductors separated by dielectric material over a part of their length, said dielectric material being formed by earth, sand, gravel, or a combination thereof as filling material, the reinforcements extending mainly in a longitudinal direction (X) from the construction facing, and being substantially parallel spaced apart by a distance D being comprised between 0.2 m and 3 m, in which the reinforcements are mechanically connected to the facing,
a plurality of auxiliary electrical conductors which, each of them, electrically links a reinforcement to an electrical contact electrically accessible from the outer surface of the facing, and
an electronic apparatus configured to emit an incident signal applied via the electrical contacts to the ends of the pair of two conductors and to collect reflected signals measured at the terminals of the first ends of the pair of two conductors with the opposed second ends being not electrically coupled to one another, and to analyze the reflected signals so as to deduce therefrom the presence of a localized potential structural defect on the first reinforcement, and the location of this defect along the first reinforcement.

16. The system for monitoring a civil engineering construction as claimed in claim 15, in which the electronic apparatus comprises a network analyzer.

17. The system for monitoring a civil engineering construction as claimed in claim 15, wherein each of the electrical contacts is electrically coupled to the reinforcement via an anchor inserted in the casting of a concrete panel forming part of the facing, said anchor mechanically coupling the reinforcement to the facing.

18. The system as claimed in claim 15, wherein the electrical contact is housed in a connector protected from the environment, received in a hollow formed in the frontage of the facing.

* * * * *